US00PP13441P2

(12) United States Plant Patent
McDonald et al.

(10) Patent No.: US PP13,441 P2
(45) Date of Patent: Dec. 31, 2002

(54) POLEMONIUM PLANT NAMED 'SNOW AND SAPPHIRES'

(75) Inventors: Floyd McDonald, Fairview, TN (US); Daniel M. Heims, Portland, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 10/032,028

(22) Filed: Dec. 20, 2001

(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—A Para
(74) *Attorney, Agent, or Firm*—Klarquist Sparkman, LLP

(57) ABSTRACT

A new and distinct hybrid of *Polemonium caeruleum* plant characterized by vigor and variegated leaves.

2 Drawing Sheets

The present invention relates to a new and distinct cultivar of *Polemonium caeruleum*, of the family Polemoniaceae, which originated as a chance seedling found by Floyd McDonald in a sowing of *Polemonium caeruleum*.

The new variety has been reproduced only by asexual propagation (division and tissue culture). Each of the progeny exhibits identical characteristics to the original plant.

This plant is characterized by the following:

1. Beautiful, stable, variegated foliage that persists all summer to frost.
2. Excellent vigor and heat tolerance.
3. Good size blue flowers.

Asexual propogation by tissue culture using standard micropropagation techniques with terminal and lateral shoots as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

DETAILED PLANT DESCRIPTION

Figure 1:
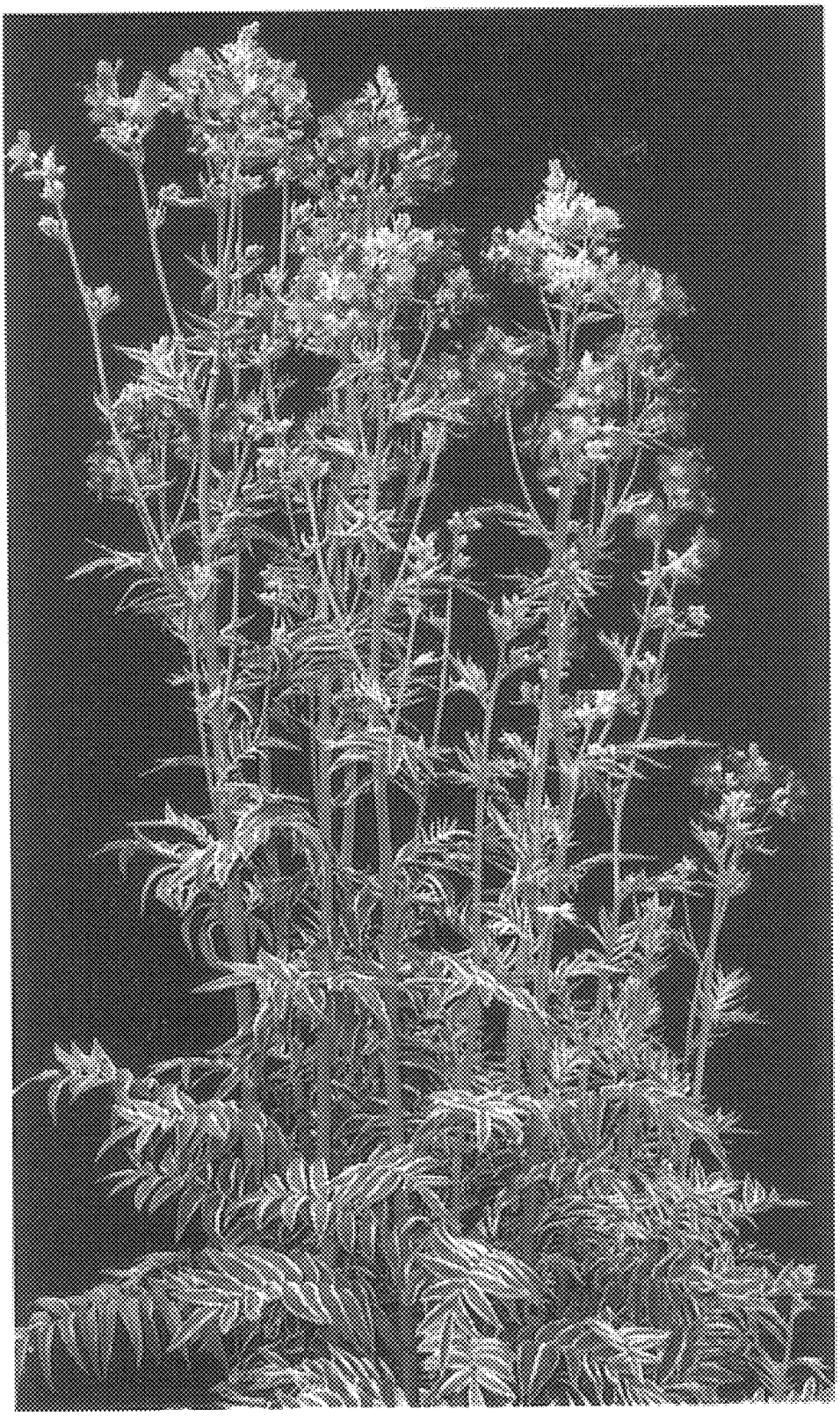
FIG. 1 shows Polemonium 'Snow and Sapphires' growing in the garden in Canby, Oreg.
Figure 2:
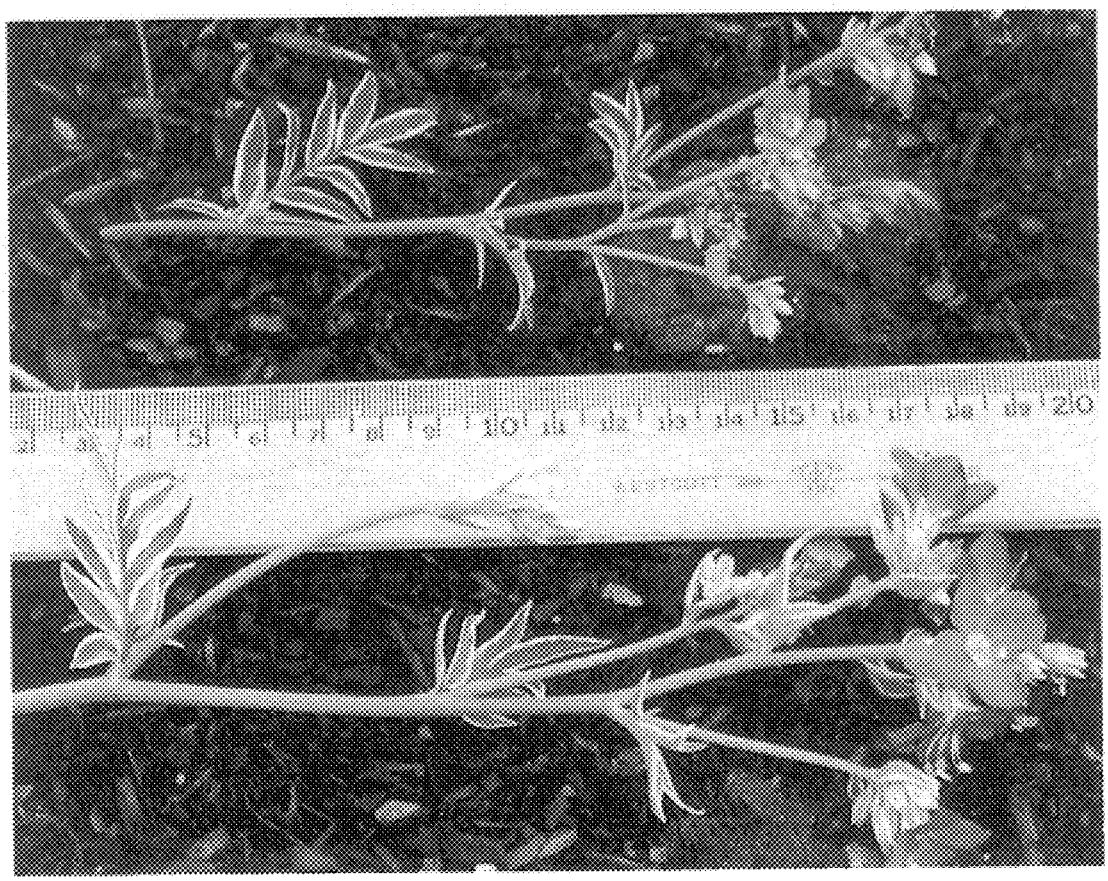
FIG. 2 shows a comparison of a flowering branch of Polemonium 'Brise d'Anjou' (top) with the new cultivar (bottom).

The following is a detailed description of the new Polemonium hybrid based on observations of a one-and-a half-year-old specimen grown in the garden in Canby, Oreg. The color description are all based on The Royal Horticultural Society Colour Chart.

Botanical classification: *Polemonium caeruleum.*
Market class: Herbaceous perennial.
Plant:
- *Type.*—Herbaceous perennial.
- *Hardiness.*—USDA Zones 5 to 9.
- *Size.*—40 cm. wide and 90 cm. tall when in full bloom.
- *Form.*—Basal clump.

Leaf:
- *Type.*—Pinnately compound. Odd pinnate with 19 to 24.
- *Shape.*—Leaflets ovate.
- *Arrangement.*—Rosette, cauline leaves alternate.
- *Length.*—8 to 15 cm.
- *Width.*—6 to 7 cm. at the widest part.
- *Leaflet.*—Shape — Ovate. Margins — Entire. Apex — Acute to acuminate. Base — Attenuate.
- *Texture.*—Glabrous with villous hairs on rachis.
- *Venation.*—Pinnate.
- *Petiole length.*—7cm to sessile, clasping at the base.
- *Petiole texture.*—Glabrous.
- *Petiole color.*—Yellow Green 146B or 147B.
- *Color.*—Grey green with creamy margins. Topside — Closest to Yellow Green 147A with margins Yellow 4D. Bottom — Greyed Green 194A with margins Yellow 4D.

Inflorescence:
- *Type.*—Terminal corymbose cyme.
- *Peduncle.*—Height: 75 cm. Diameter: 0.7 cm. Texture: Glandular pubescent. Color: Yellow Green 146C.
- *Pedicel.*—Length: 0.4 cm. Texture: Glandular pubescent. Color: Yellow Green 146B.
- *Flower number.*—160 per peduncle.

Flower bud:
- *Size.*—0.9 cm. deep and 0.6 cm. wide.
- *Shape.*—Plicate.
- *Color.*—Violet Blue 90A.

Flower:
- *Type.*—Zygomorphic.
- *Shape.*—Rotate with lobe length exceeding tube length.
- *Size.*—2.4 cm wide and 1.3 cm deep.
- *Corolla.*—5 fused petals. Lobes 0.9 cm long and 0.8 cm wide, ovate, rounded with and acute tip.
- *Texture.*—Satiny.
- *Color.*—Violet Blue 90A.
- *Calyx.*—5 lobes, divided ½ way to the base, glandular pubescent.
- *Calyx size.*—0.7 cm deep 0.6 cm wide.
- *Calyx color.*—Yellow Green 146B with white margins (White 155A).
- *Style.*—1.3 cm. long, purple Violet 82A.
- *Stigma.*—3 parted, Greyed Green 197C.
- *Stamen number.*—5.
- *Filaments.*—1.3 cm long, Violet Blue 91B.

*Pollen color.*—Yellow 11A.

*Bloom period.*—May through July and again in September if the old flowering stems are removed.

*Fragrance.*—Sweet.

Fruit:

*Type.*—Ovoid 3-valved capsule.

*Color.*—Tan, Grey Brown 199D.

*Size.*—0.3 cm wide and 0.4 cm deep.

Seed:

*Fertility.*—Good.

*Size.*—2.5 mm long.

*Shape.*—Sickle.

*Color.*—Brown 200A.

Disease: None observed on plant grown under commercial conditions in Canby, Oreg.

COMPARISONS TO SIMILAR POLEMONIUM

Compared to Polemonium 'Brise d'Anjou' (U.S. Plant Pat. No. 9,781), this new cultivated variety has more vigor and is taller, with bigger, darker flowers. The leaf color is a grayer green with a cream rather than light yellow margin. This new cultivar withstands heat and humidity, which causes Polemonium 'Brise d'Anjou' to die back.

I claim:

1. A new and distinct hybrid of *Polemonium caeruleum* plant substantially as shown and described, characterized by vigor and leaf variegation.

* * * * *